United States Patent
Auerbach et al.

(10) Patent No.: US 11,246,534 B2
(45) Date of Patent: Feb. 15, 2022

(54) BASKET CATHETER MADE FROM FLEXIBLE CIRCUIT BOARD WITH MECHANICAL STRENGTHENING

(71) Applicant: BIOSENSE WEBSTER (ISRAEL) LTD., Yokneam (IL)

(72) Inventors: Shmuel Auerbach, Kerem Maharal (IL); Avi Reuveni, Givat Shmuel (IL); Toam Shemesh, Hertziliya (IL); Michael Levin, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1395 days.

(21) Appl. No.: 15/412,436

(22) Filed: Jan. 23, 2017

(65) Prior Publication Data
US 2018/0206792 A1    Jul. 26, 2018

(51) Int. Cl.
*A61B 5/00*    (2006.01)
*A61B 5/287*    (2021.01)

(52) U.S. Cl.
CPC ............ *A61B 5/6858* (2013.01); *A61B 5/287* (2021.01); *A61B 5/6859* (2013.01)

(58) Field of Classification Search
CPC ..... A61B 5/042; A61B 5/6858; A61B 5/6859; A61B 5/0422; A61B 18/12; A61B 18/1492; A61B 2018/00595; A61B 5/287; A61M 2025/0063
See application file for complete search history.

(56) References Cited

U.S. PATENT DOCUMENTS

| | | |
|---|---|---|
| 5,391,199 A | 2/1995 | Ben-Haim |
| 5,772,590 A | 6/1998 | Webster, Jr. |
| 5,823,189 A | 10/1998 | Kordis |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim |

(Continued)

FOREIGN PATENT DOCUMENTS

| | | |
|---|---|---|
| WO | WO 96/05768 A1 | 2/1996 |
| WO | WO 2014/124231 A1 | 8/2014 |
| WO | WO 2016/065464 A1 | 5/2016 |

OTHER PUBLICATIONS

Mazzuferi, Manuela et al., "The biocompatibility of materials used in printed circuit board technologies with respect to primary neuronal and K562 cells", Biomaterials, Feb. 2010, pp. 1045-1054, vol. 31, Issue 6.

(Continued)

*Primary Examiner* — Eun Hwa Kim (57) ABSTRACT

A catheter includes a shaft for insertion into an organ of a patient, an extendable distal-end assembly, and two or more strengthening elements. The extendable distal-end assembly is coupled to the shaft and includes multiple splines, at least one spline includes a flexible circuit board having one or more electrodes disposed thereon, the circuit board is configured, when the distal-end assembly is extended in the organ, to conform to a surface of the organ so as to make contact between the electrodes and the surface. The strengthening elements are distributed along the circuit board of the spline and are configured to mechanically strengthen the spline.

14 Claims, 5 Drawing Sheets

(56) References Cited

U.S. PATENT DOCUMENTS

| | | | |
|---|---|---|---|
| 7,799,014 | B2 | 9/2010 | McGuckin, Jr. et al. |
| 8,504,133 | B2 | 8/2013 | Kordis et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2004/0101644 | A1 | 5/2004 | Kinoshita et al. |
| 2009/0171274 | A1* | 7/2009 | Harlev ................ A61B 5/0422 |
| | | | 604/95.04 |
| 2014/0243879 | A1* | 8/2014 | Rothstein ................ A61F 2/013 |
| | | | 606/200 |
| 2015/0342491 | A1 | 12/2015 | Marecki et al. |
| 2015/0366508 | A1* | 12/2015 | Chou ................ A61B 18/1492 |
| | | | 600/374 |
| 2016/0242667 | A1 | 8/2016 | Fay et al. |
| 2016/0353584 | A1* | 12/2016 | Honda ................ H05K 3/426 |

OTHER PUBLICATIONS

European Search Report dated May 25, 2018, Application No. EP 18 15 2759.
European Search Report dated Oct. 1, 2020, Application No. EP 20 18 2889.

* cited by examiner

BASKET CATHETER MADE FROM FLEXIBLE CIRCUIT BOARD WITH MECHANICAL STRENGTHENING

FIELD OF THE INVENTION

The present invention relates generally to catheters, and particularly to methods and systems for strengthening catheters made from flexible circuit boards.

BACKGROUND OF THE INVENTION

Basket catheters may be used in various medical applications, such as cardiology. Several types of basket catheters, structured with multiple splines, are designed to enable sensing and treating of arrhythmia.

For example, U.S. Pat. No. 8,504,133, whose disclosure is incorporated herein by reference, describes a system for sensing multiple local electrical voltages from endocardial surface of a heart. The system includes an elongate tubular member; a plurality of flexible splines having proximal portions, distal portions and medial portions therein between; an anchor for securely affixing the proximal portions of the splines; an atraumatic tip for securely affixing the distal portions of the splines; and a polymeric member including opposed a first open end and a second open end defining an open lumen therein between and an inner member surface and an outer member surface.

U.S. Pat. No. 5,722,401, whose disclosure is incorporated herein by reference, describes a catheter probe comprising a flexible elongate tubular member having proximal and distal extremities. An expandable assembly capable of moving from a contracted position to an expanded position is secured to the distal extremity of the flexible elongate tubular member and is formed from at least two elongate members movable between contracted and expanded positions.

U.S. Patent Application Publication 2015/0366508, whose disclosure is incorporated herein by reference, describes a flex-PCB catheter device that comprises an elongate shaft, an expandable assembly, a flexible printed circuit board (flex-PCB) substrate, a plurality of electronic components and a plurality of communication paths.

SUMMARY OF THE INVENTION

An embodiment of the present invention that is described herein provides a catheter including a shaft for insertion into an organ of a patient, an extendable distal-end assembly, and two or more strengthening elements. The extendable distal-end assembly is coupled to the shaft and includes multiple splines, at least one spline includes a flexible circuit board having one or more electrodes disposed thereon, the circuit board is configured, when the distal-end assembly is extended in the organ, to conform to a surface of the organ so as to make contact between the electrodes and the surface. The strengthening elements are distributed along the circuit board of the spline and are configured to mechanically strengthen the spline.

In some embodiments, the strengthening elements include stripes coupled to the circuit board. In other embodiments, the electrodes are coupled to a side of the circuit board facing the surface of the organ. In yet other embodiments, the strengthening elements are coupled to a side of the circuit board not facing the surface of the organ.

In an embodiment, the strengthening elements include two or more blocks coupled to the circuit board. In another embodiment, at least a pair of adjacent blocks includes respective magnets that are positioned so as to magnetically repulse one another. In yet another embodiment, at least one of the blocks has a trapezoid shape.

In some embodiments, the catheter includes one or more elastic wedges, each wedge is coupled between two adjacent blocks and is configured to force the spline to conform to the surface of the organ. In other embodiments, the blocks are made from aramid fiber-filled epoxy (AFEP). In yet other embodiments, the circuit board is made from one or more layers of Kapton.

In an embodiment, the catheter includes a basket catheter.

There is additionally provided, in accordance with an embodiment of the present invention, a method for producing a catheter, the method including providing a spline, which includes a flexible circuit board having one or more electrodes disposed thereon. Two or more strengthening element are distributed along the circuit board of the spline, so as to mechanically strengthen the spline. An extendable distal-end assembly that includes multiple splines is produced, at least one of the splines includes the spline. The distal end assembly is coupled to a shaft for inserting the catheter into an organ of a patient.

There is further provided, in accordance with an embodiment of the present invention, a method for applying a medical procedure, the method including inserting into an organ of a patient a catheter including a distal-end assembly, which includes multiple splines, of which at least one spline includes: a flexible circuit board having one or more electrodes disposed thereon, and two or more strengthening elements, which are distributed along the circuit board of the spline so as to mechanically strengthen the spline. The distal-end assembly is extended inside the organ to allow the splines to conform to a surface of the organ so as to make contact between the electrodes and the surface. The medical procedure is applied using the electrodes.

The present invention will be more fully understood from the following detailed description of the embodiments thereof, taken together with the drawings in which:

DETAILED DESCRIPTION OF EMBODIMENTS

Overview

Embodiments of the present invention that are described hereinbelow provide improved configurations of distal-end assemblies used in medical catheters. In some embodiments, a distal-end assembly of a catheter comprises multiple splines, wherein each spline comprises a strip of flexible circuit board typically made from Kapton™. In an embodiment, various kinds of electrodes and other devices may be disposed on the circuit board side facing the patient tissue, wherein the circuit board provides electrical connectivity between the electrodes and wiring running through the catheter.

The catheter is typically inserted into the patient body in a collapsed position (e.g., using a sheath) and extended upon reaching a target location such as a cavity of an organ in question. In some embodiments, in the collapsed position, the external diameter of the catheter in the sheath does not exceed a certain size (e.g., 3.17 mm), so as to enable navigation of the catheter in the patient body (e.g., along blood vessels). In an embodiment, the splines are designed so as not to deform while being tightened in the sheath during navigation. In the extended position, the splines are extended to conform to the shape of the cavity so that the electrodes disposed on the splines come into contact with the tissue of the inner cavity surface.

In some embodiments, at least one of the splines comprises two of more strengthening elements that are distributed along the circuit board of the spline so as to mechanically strengthen the spline. The strengthening elements are configured to prevent deformation of the spline in the collapsed position, and to enable firm and reliable contact between the spline electrodes and the organ tissue in the extended position.

In some embodiments, one or more stripes (e.g., additional flexible circuit boards or circuit-board layers) may be coupled to the circuit board so as to mechanically strengthen the spline. In other embodiments, the strengthening elements may comprise two or more blocks coupled to the circuit board without touching the tissue.

In various embodiments, the cross-section of the blocks may have any suitable shape, such as a trapezoid shape. In another embodiment, each block may further comprise a magnetic element. The magnetic elements in adjacent blocks may be arranged to magnetically repulse one another, thereby applying a straightening force to the spline in the extended position.

The disclosed techniques are particularly effective in multi-spline catheters that are required to carry a large number of electrodes and sensors. Using circuit board splines enables miniaturization of the electrodes and simplifies the electrical connectivity between the electrodes and the proximal end of the catheter. Furthermore, the disclosed techniques may reduce the need to build the catheter splines from expensive materials, such as nickel titanium (nitinol), therefore reducing the cost of such catheters and related medical procedures.

System Description

Figure 1:
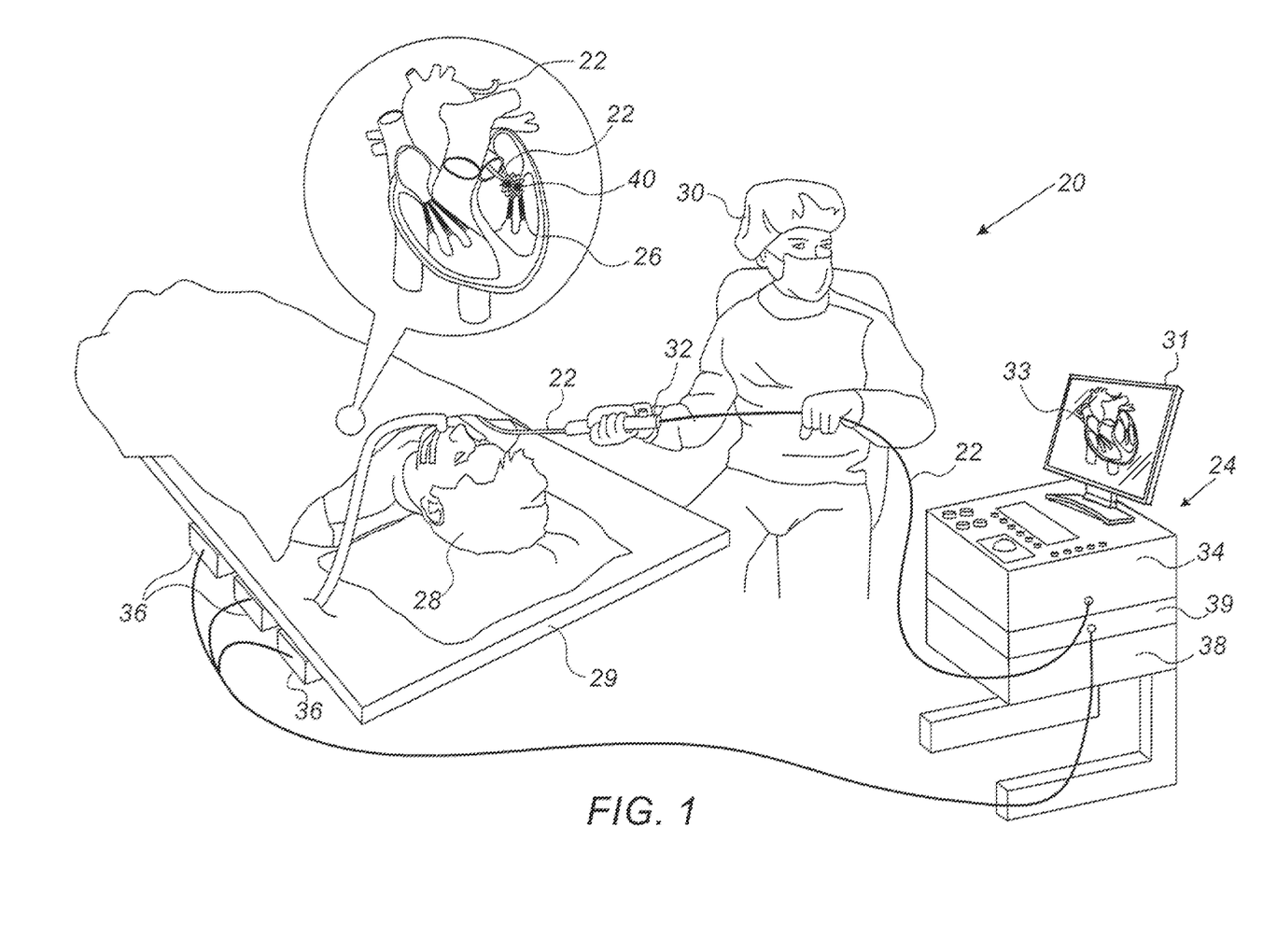
FIG. 1 is a schematic, pictorial illustration of a catheter tracking system, in accordance with an embodiment of the present invention.

FIG. 1 is a schematic, pictorial illustration of a catheter tracking system 20, in accordance with an embodiment of the present invention. System 20 comprises a probe 22, in the present example a cardiac catheter, and a control console 24. In the embodiment described herein, catheter 22 may be used for any suitable therapeutic and/or diagnostic purposes, such as ablation of tissue in a heart 26 and the mapping of electro-cardiac signals for the diagnosis of cardiac dysfunctions, such as cardiac arrhythmias, for example.

Console 24 comprises a processor 39, typically a general-purpose computer, with suitable front end and interface circuits for receiving signals from catheter 22 and for controlling the other components of system 20 described herein. Processor 39 may be programmed in software to carry out the functions that are used by the system, and the processor stores data for the software in a memory 38. The software may be downloaded to console 24 in electronic form, over a network, for example, or it may be provided on non-transitory tangible media, such as optical, magnetic or electronic memory media. Alternatively, some or all of the functions of processor 39 may be carried out by dedicated or programmable digital hardware components.

An operator 30 (such as an interventional cardiologist) inserts catheter 22 through the vascular system of a patient 28 lying on a table 29. Catheter 22 comprises an insertion tube, and a distal-end assembly 40 that comprises multiple splines (shown in FIG. 2). Operator 30 moves assembly 40 of catheter 22 in the vicinity of the target region in heart 26 by manipulating catheter 22 with a manipulator 32 near the proximal end of the catheter as shown in the inset of FIG. 1. The proximal end of catheter 22 is connected to interface circuitry in processor 39.

The position of the distal-end assembly in the heart cavity is typically measured by magnetic position sensing in catheter tracking system 20. In this case, console 24 comprises a driver circuit 34, which drives magnetic field generators 36 placed at known positions external to patient 28 lying on table 29, e.g., below the patient's torso.

Distal-end assembly 40 typically comprises multiple splines, each comprising one or more magnetic field sensors and/or one or more ablation or mapping electrodes, and/or other devices (as shown, for example in FIGS. 2 and 3 below). When the distal-end assembly is brought into contact with the intracardiac tissue, e.g., the inner heart surface, the mapping electrodes generate potential gradient signals in response to the sensed electrical potentials and the position sensors generate position signals in response to the sensed external magnetic fields, thereby enabling processor 39 to map the electrical potentials as a function of position within the heart cavity.

The multiple magnetic position sensors and mapping electrodes in assembly 40 are connected to interface circuitry in processor 39 at the catheter proximal end. Operator 30 can view the position of assembly 40 in an image 33 of heart 26 on a user display 31.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In other embodiments, instead of magnetic position sensors, distal end assembly 40 may comprise one or more impedance position sensors, such as advanced current localization (ACL) sensors, or any other suitable position sensors, and system 20 comprises a respective position tracking module. In alternative embodiments, system 20 does not comprise any position tracking module, and distal end assembly 40 does not comprise any position tracking sensors.

Figure 2:
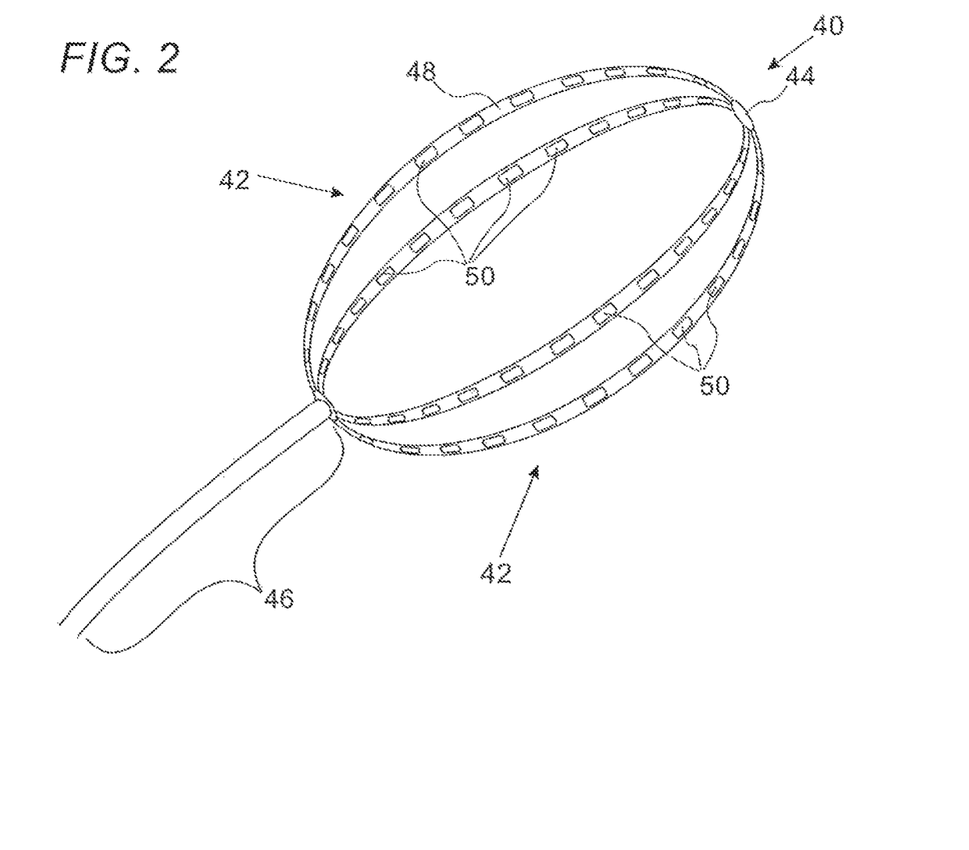
FIG. 2 is a schematic, pictorial illustration of a distal-end assembly in an extended position, in accordance with an embodiment of the present invention.

FIG. 2 is a schematic, pictorial illustration of distal-end assembly 40 in an extended position, in accordance with an embodiment of the present invention. Assembly 40 comprises one or more splines 42. Each spline 42 comprises an arm that is flexible about its longitudinal axis. Arm 42 may each be fabricated from a strip of flexible circuit board 48 made from Kapton™, or from any other suitable material that allows bending the splines of assembly 40 as required at the collapsed and extended positions. During the insertion of the catheter, splines 42 are grouped together in a collapsed position (as will be depicted in FIG. 6 below) and held within a sheath, or any other suitable device. After inserting the catheter distal end into the cavity of interest, the splines are set to an extended position as shown in FIG. 2.

In some embodiments, board 48 may have a length of 80.9 mm, a width of 11.25 mm and a thickness of about 0.18 mm. In other embodiments, any other suitable dimensions may be applied.

Each spline 42 typically comprises one or more embedded electrodes 50, such as mapping electrodes, position sensors, tissue ablation electrodes, or any other suitable type of electrodes. In the extended position, one or more of splines 42 are in contact with the inner heart surface in order to collect signals from the heart tissue, or to apply signals to the heart tissue, using the electrodes.

Assembly 40 further comprises a distal cap 44 located at a distal-end of assembly 40. Assembly 40 additionally comprises a shaft 46, which is used for the transition of assembly 40 between the collapsed and extended positions.

In an embodiment, cap 44 comprises an atraumatic tip made from polished steel or nitinol for securely navigating assembly 40 in heart 26. The distal sections of the splines couple together to the cap, as also depicted in FIGS. 3 and 4 below.

Figure 10A:
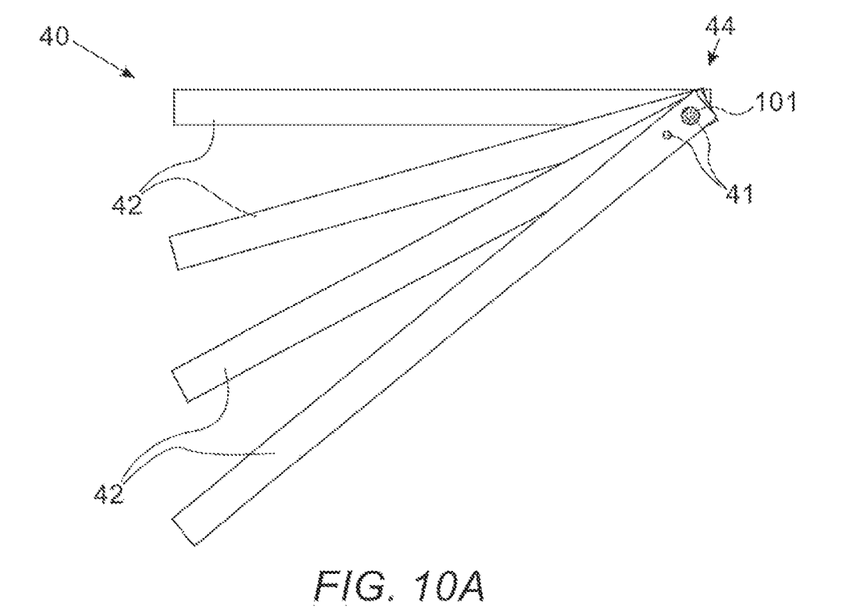
FIGS. 10A and 10B are schematic, pictorial illustrations of distal caps of a distal-end assembly, in accordance with embodiments of the present invention.
Figure 10B:
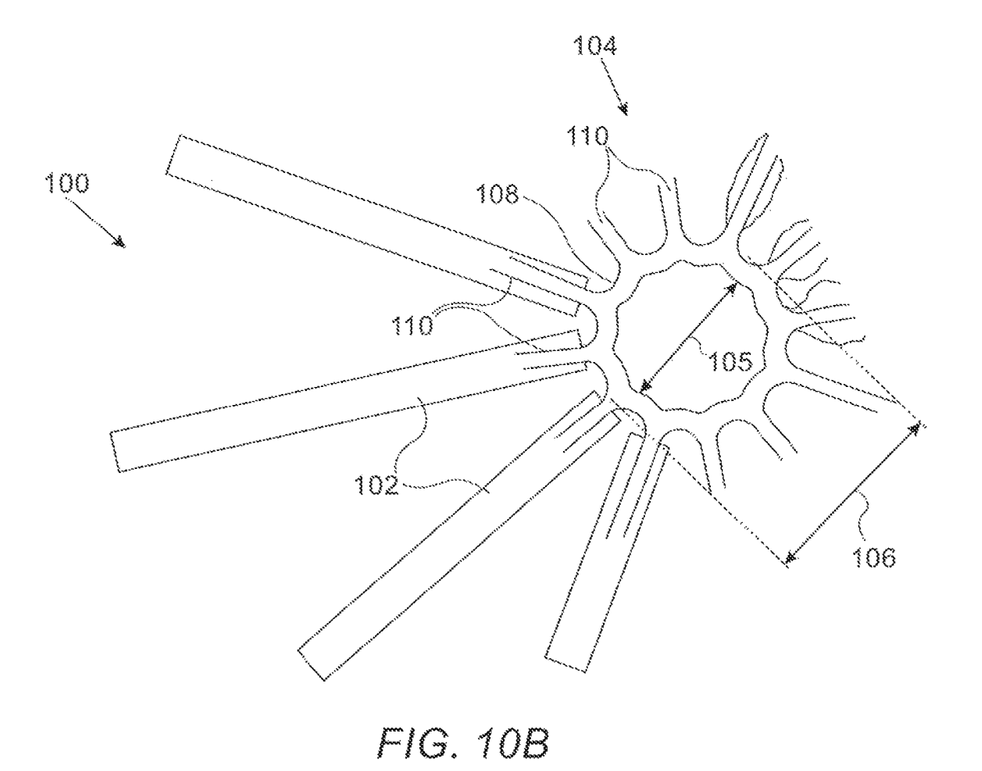

Cap 44 and shaft 46 may be fabricated from a suitable polished steel or nitinol, or any other suitable material, and are configured to couple the proximal and distal ends of splines 42, respectively. In the extended position, shaft 46 is pushed toward cap 44, thereby bending splines 42 as shown in FIG. 2. In some embodiments, cap 44 may be configured in one of two configurations that are depicted in FIG. 10 below.

Figure 3:
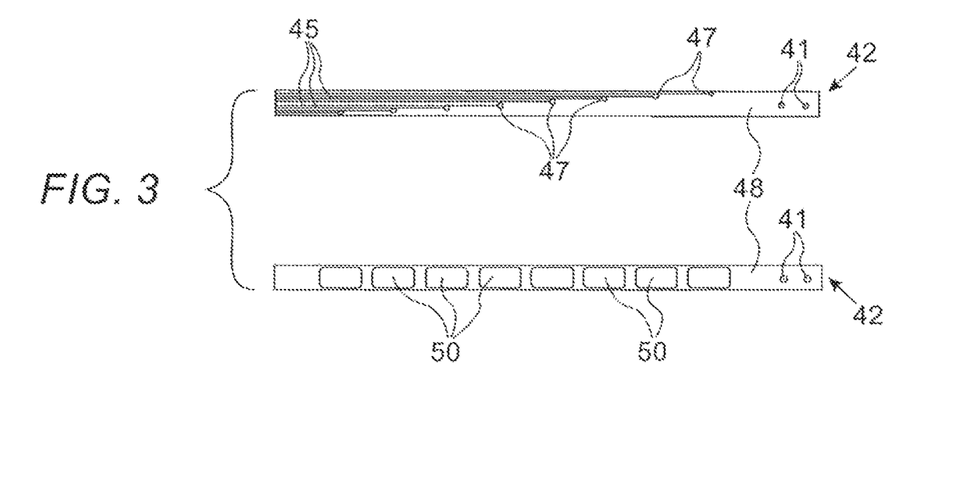
FIG. 3 is a schematic, pictorial illustration of a spline of a distal-end assembly, in accordance with an embodiment of the present invention.
Figure 4:
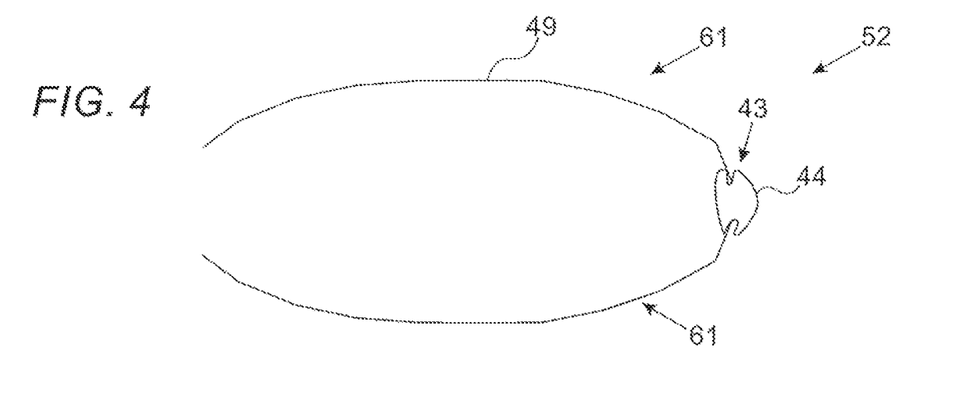
FIGS. 4, 5, 7 and 8 are schematic, sectional views of distal-end assemblies in an extended position, in accordance with embodiments of the present invention.

FIG. 3 is a schematic, pictorial illustration of top and bottom views of spline 42, in accordance with an embodiment of the present invention. The upper part of FIG. 3 represents a bottom view, showing the lower surface of spline 42, and the lower part of FIG. 3 represents a top view, showing the upper surface of the same spline. When the catheter is deployed, the upper surface of spline 42 faces the cavity tissue and the lower surface faces away from the tissue.

In some embodiments, spline 42 is perforated with one or more anchoring holes 41 used for coupling spline 42 to cap 44 during the production of distal end 40.

In some embodiments, multiple electrodes 50 are formed on the upper surface of board 48 so that in the extended position of distal end 40, as depicted in FIG. 2, electrodes 50 make contact with the tissue of heart 26. Other components, such as sensors, may be coupled to the spline in a similar manner.

In some embodiments, electrical circuit traces 45 are formed on the lower surface of spline 42, each trace 45 is connected to an electrode 50 at a respective contact 47. In an embodiment, each contact 47 comprises a plated conductive via that passes through the circuit board to the upper surface and connects the respective trace 47 to the respective electrode 50. In other embodiments, the contacts and traces may be arranged in another suitable configuration, such as the configuration that will be depicted in FIG. 9 below.

In some embodiments, circuit traces 45 are connected to suitable wiring that runs through the catheter, for exchanging signals between console 24 and electrodes 50. For example, traces 45 may be used for sending electropotential (EP) signals sensed in heart 26 by electrodes 50 to console 24.

Mechanical Strengthening of Splines

In the extended position, it is important that the electrodes on the splines of the distal-end assembly make reliable contact with the inner surface of heart 26 so as to collect signals from the heart tissue, or apply signals to the heart tissue, using the electrodes. In some cases, a spline may be deformed due to its flexibility, in which case some of the electrodes may not be in contact with the inner surface. Therefore, it is important to mechanically strengthen the splines so as to ensure that each spline conforms to the inner surface of heart 26. Embodiments of the present invention that are described herein depict methods and apparatus for mechanically strengthening the splines.

FIG. 4 is a schematic, sectional view of a distal-end assembly 52 in an extended position, in accordance with an embodiment of the present invention. Assembly 52 may replace, for example, assembly 40 of FIG. 2 above.

In some embodiments, assembly 52 comprises multiple splines 61 that are made from strips of Kapton or any other suitable substrate material for producing a flexible board 49. In an embodiment, board 49 may replace, for example, board 48 of FIG. 2 above. Board 49 may comprise electrodes (not shown), such as electrodes 50 depicted in FIG. 2 above.

In some embodiments, spline 61 comprises two or more Kapton boards coupled to one another, e.g., using gluing or any other coupling techniques known in the art. The multi-layered structure of the Kapton boards may improve the stiffness of spline 61 so that spline 61 well conforms to the inner surface of heart 26 to make direct contact between the spline electrodes and the inner surface.

In some embodiments, spline 61 further comprises a coupling mechanism 43 adapted to couple spline 61 to cap 44. In an embodiment, mechanism 43 comprises one or more anchoring holes 41 or any other mechanism suitable for coupling spline 61 to cap 44. In some embodiments, cap 44 may have either of two configurations that are depicted in FIGS. 10A and 10B below.

Figure 5:
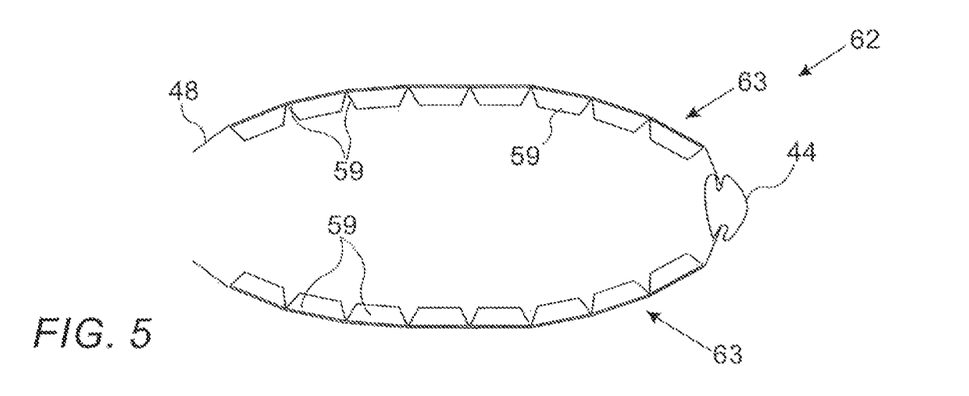

FIG. 5 is a schematic, sectional view of a distal-end assembly 62 in an extended position, in accordance with another embodiment of the present invention. Assembly 62 may replace, for example, assembly 40 of FIG. 2 above.

In some embodiments, assembly 62 comprises one or more splines 63 that may replace, for example, splines 42 in FIG. 2 above. In an embodiment, spline 63 comprises board 48 comprising one or more layers of Kapton (typically up to three layers), and having electrodes (not shown) such as electrodes 50 as depicted in FIG. 2 above.

In some embodiments, spline 63 further comprises one or more strengthening elements 59, also referred to as "blocks." In an embodiment, each element 59 is made from aramid fiber-filled epoxies F161 cured (AFEP) or from any other suitable material, and has a trapezoid shape or any other suitable shape.

In an embodiment, the length of the trapezoid long base is about 5 mm, and the length of its short base is about 0.72 mm. The trapezoid has a typical thickness of 0.25 mm, and a typical angle between the long base of the trapezoid and its side edges is 40.5 degrees. The large base of the trapezoid is coupled to the lower surface of board 48 so as to mechanically strengthen spline 63.

In some embodiments, multiple elements 59 are coupled in a row along the lower surface of board 48 next to one another, whereas the large bases are in close proximity (or in physical contact) with one another. In some embodiments, the trapezoid shape and the arrangement of elements 59 limit the curvature of spline in the extended position, as will be described in detail in FIG. 6 below.

The configuration of splines 63 and elements 59 in FIG. 5 is depicted purely by way of example. In alternative embodiments, any other suitable configuration may be used. For example, spline 63 may have the electrodes coupled only at the center of the upper surface of board 48, in which case, elements 59 may be coupled only at the center of the lower surface of board 48, so as to enable shrinking assembly 62 (as depicted in FIG. 6 below) and to ensure that the electrodes are in contact with the inner wall of heart 26.

Figure 6:
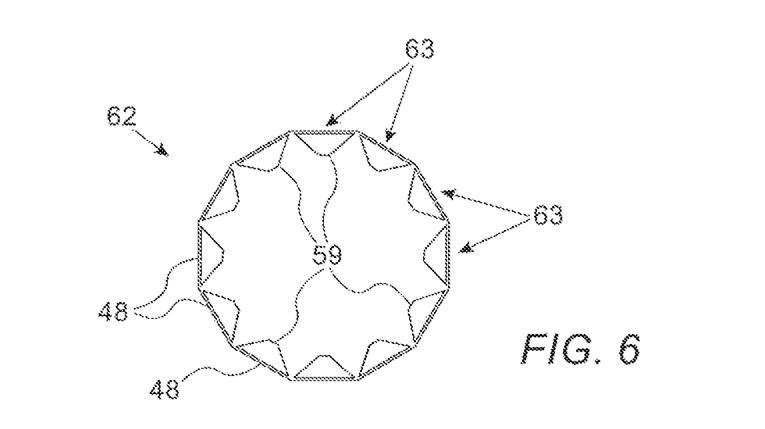
FIG. 6 is a schematic, sectional view of a distal-end assembly in a collapsed position, in accordance with an embodiment of the present invention.

FIG. 6 is a schematic, sectional view of distal-end assembly 62 of FIG. 5 in a collapsed position, in accordance with an embodiment of the present invention. The sectional view depicted in FIG. 6 is viewed frontally, from the distal end of assembly 62.

In the example of FIG. 6, assembly 62 comprises twelve splines 63, wherein each spline comprises board 48 to which coupled a single element 59. As described above, during the insertion of catheter 22, the splines are grouped together in a collapsed position and held in a sheath.

In an embodiment, the shape and dimensions of element 59 determine the minimal diameter of assembly 62 in the collapsed position. The diameter of assembly 62 in the collapsed position is typically dictated by the width of the blood vessels leading to the organ in question. For example, a typical diameter of a blood vessel of a human heart is 3-4 mm, therefore, the typical external diameter of assembly 62 is between 7 French and 9.5 French (equivalent to 2.33 mm-3.17 mm) depends on the amount of electrodes disposed on the splines.

In the example of FIG. 6, the minimal diameter of assembly 62 in a collapsed position is limited by the size of the small base of the trapezoid. Assembly 62 cannot shrink any further when the small bases of adjacent elements are in physical contact with one another. This attribute determines the number of splines per assembly, and dictates the shape and dimensions of elements 59. The minimal diameter of assembly 62, when collapsed, may also be impacted by elements such as sensors, interconnection wiring, irrigation tubes or other elements.

Figure 7:
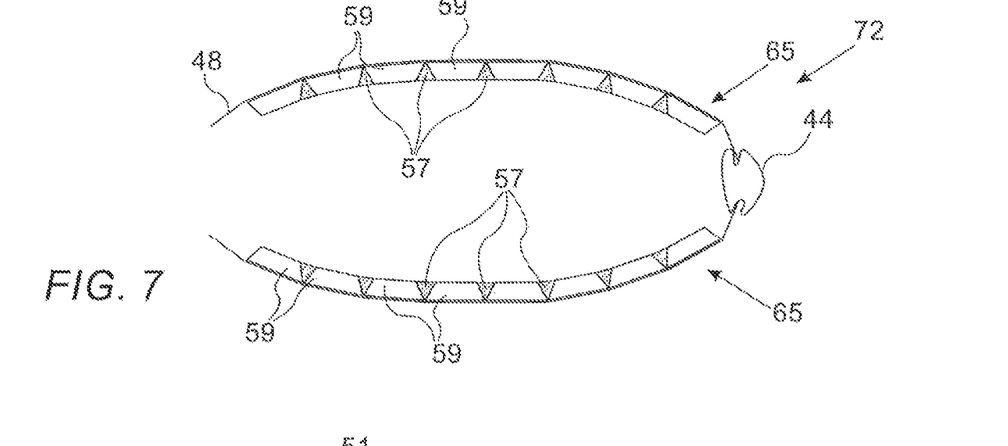

FIG. 7 is a schematic, sectional view of a distal-end assembly 72 in an extended position, in accordance with yet another embodiment of the present invention. Assembly 72 may replace, for example, assembly 40 of FIG. 2 above.

In some embodiments, assembly 72 comprises one or more splines 65, each spline 65 may replace, for example, spline 42 in FIG. 2 above. In an embodiment, spline 65 has a similar basic structure as spline 63 with elements 59, and further comprises one or more elastic wedges 57. Each wedge 57 is typically made from silicone rubber to make it elastic, and is coupled (e.g., glued) to two adjacent elements 59 using polyurethane (PU) or any other suitable glue. In some embodiments, wedge 57 may have a pyramid shape. An exemplary height of the pyramid is 0.23 mm, and exemplary length and width of the pyramid rectangular base are 0.72 mm and 0.25 mm, respectively.

In an embodiment, the elastic wedges are compressed when the distal-end assembly is in the collapsed position, and stretched or relaxed when the distal-end assembly is in the extended position.

In some embodiments, wedges 57 further limit the shrinkage of assembly 72 (e.g., in a collapsed position) by filling the space between elements 59. In an embodiment, wedges 57 may stretch to a limited extent in the extended position, thereby limiting the maximal diameter of assembly 72 in the extended position.

In the example of FIG. 7, wedge 57 has a triangular shape that fills the volume between adjacent diagonals of the respective adjacent elements 59. In other embodiments, any other suitable shape of elements 59 and wedges 57 may be used so as to improve the conformance of splines 65 with the cavity tissue (e.g., inner wall of heart 26), and to limit the allowable shrinkage of assembly 72 (and thus, the maximal deformation of splines 65).

Figure 8:
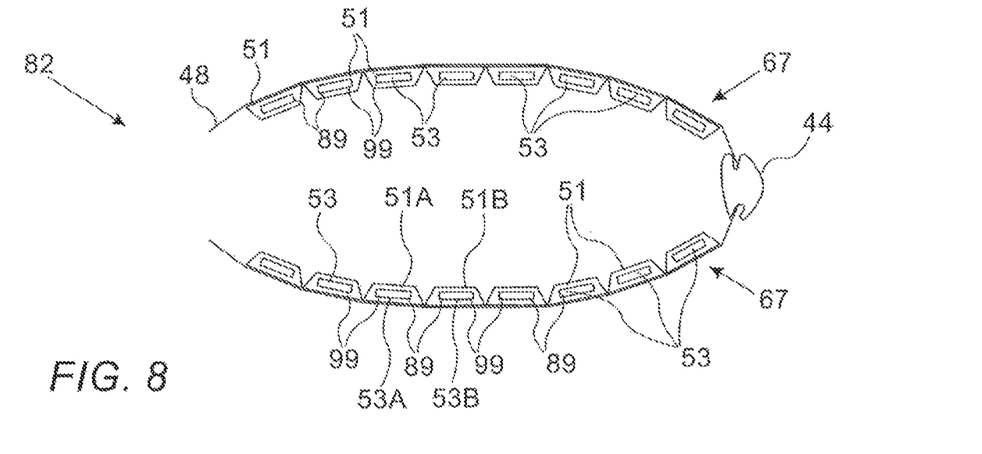

FIG. 8 is a schematic, sectional view of a distal-end assembly 82 in an extended position, in accordance with an embodiment of the present invention. Assembly 82 may replace, for example, assembly 40 of FIG. 2 above.

In some embodiments, assembly 82 comprises one or more splines 67, each spline 67 may replace, for example, spline 42 in FIG. 2 above. In an embodiment, spline 67 comprises one or more blocks of strengthening elements 51. In an embodiment, each element 51 is made from AFEP (substantially similar to element 59) or from any other suitable material, and may have a trapezoid shape.

In some embodiments, each element 51 comprises a magnetic element 53 having a positive pole 89 and a negative pole 99.

In some embodiments, magnetic elements 53 are made from alnico, which is an acronym for an iron bulk alloyed with aluminum, nickel and cobalt. In an embodiment, each element 53 is embedded into element 51, e.g., using a multi-step molding process. In the first step, the lower part (e.g., the long base) of element 51 is formed, then magnetic element 53 is coupled to the wide base, and next the upper part (e.g., the short base) is molded on top so as to encapsulate element 53 within element 51.

In an embodiment, magnetic elements 53 are arranged in spline 67 so that facing edges of adjacent elements 53 have the same magnetic polarity. In this arrangement, every pair of adjacent magnetic elements 53 produce a magnetic repulsion force that tends to keep them away from one another.

For example, spline 67 may comprise a strengthening element 51A, which comprises a magnetic element 53A, and a strengthening element 51B, which comprises a magnetic element 53A, whereas element 51B is located to the right side of element 51A. In an embodiment, the right edge of magnetic element 53A and the left edge of magnetic element 53B, are both positive poles 89. This arrangement forms a magnetic repulsion force between elements 51A and 51B (and between any other pair of adjacent elements 51 in spline 67), thereby straightening spline 67 to a fully extended position after being ejected out of the sheath into the heart cavity, as described in FIG. 2 above.

Figure 9:
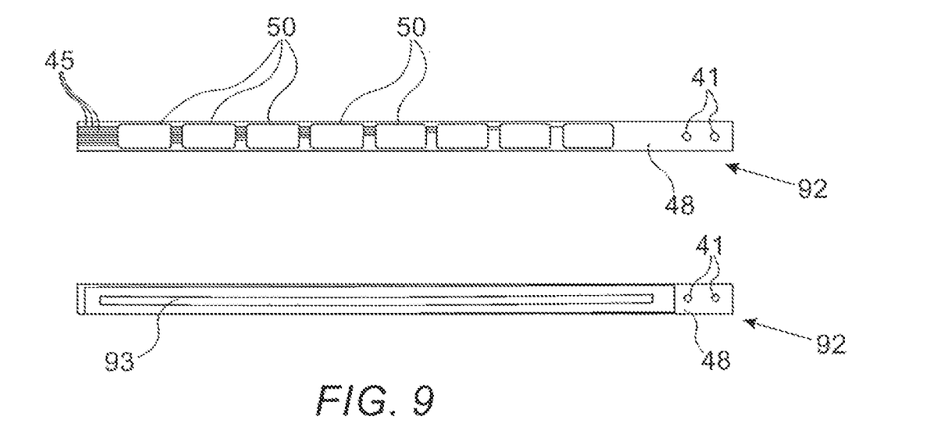
FIG. 9 is a schematic, pictorial illustration of a spline of a distal-end assembly, in accordance with another embodiment of the present invention.

FIG. 9 is a schematic, pictorial illustration of a spline 92, shown from top and bottom views, in accordance with another embodiment of the present invention.

The upper drawing of FIG. 9 represents a top view, showing the upper surface of spline 92, and the lower drawing represents a bottom view, showing the lower surface of the same spline.

Reference is now made to the top view of spline 92. In some embodiments, traces 45 and electrodes 50 are produced on the upper surface of board 48 using any production technique known in the art. An exemplary production sequence of spline 92 is described herein, but any other suitable production sequence may also be used.

Traces 45 are formed on the upper surface of board 48. One or more dielectric layers, made from polyamide or any other suitable material, are disposed on leads 45. One or more conductive connections (not shown) are formed through the dielectric material (e.g., by etching holes in the dielectric and filling the holes with conductive material, such as copper). Each connection is adapted to connect between a given trace 45 and its respective electrode 50. Therefore, the connection is formed below the intended location of the respective electrode.

Reference is now made to the bottom view of spline 92. In some embodiments, spline 92 comprises a strengthening element 93 disposed along the lower surface of board 48. Element 93 may comprise a contiguous element, such as a stripe or a fiber made from polyethylene (nylon) or any other suitable material. The fiber may be coupled to the lower surface of board 48, or embedded between the Kapton layers of board 48.

In alternative embodiments, element 93 may comprise a saline tube that may mechanically strengthen board 48, but maintain its flexibility, so as to ensure that each spline 92 conforms to the inner surface of heart 26 in the extended position.

The production of traces 45 on the upper surface of board 48 enables the use of any biocompatible material for strengthening spline 92 in the form of element 93, such as described above, or using any other suitable form.

FIG. 10A is a schematic, pictorial illustration of distal cap 44 of distal-end assembly 40 of FIG. 2, in accordance with an embodiment of the present invention. In some embodiments, each spline 42 is perforated with (e.g., two) anchoring holes 41 located at the distal end of spline 42. In an embodiment, a coupling pin 101 made of steel or any other suitable material, serves as a thread for coupling splines 42 to one another during the production of distal end 40 and during operation as described in FIG. 2 above.

FIG. 10B is a schematic, pictorial illustration of a distal cap 104 of a distal-end assembly 100, in accordance with an embodiment of the present invention. Assembly 100 may replace, for example, assembly 40 of FIG. 2 above.

In some embodiments, assembly 100 comprises multiple splines 102, each spline 102 may replace, for example, spline 63 of FIG. 5 above. In an embodiment, cap 104 comprises a ring 108 made from a suitable polished steel or nitinol, or from any other suitable material. In some embodiments, ring 108 has any suitable inner diameter 105 and outer diameter 106. For example, the inner diameter is 1.72 mm, and the outer parameter is 1.81 mm.

In an embodiment, cap 104 further comprises multiple arms 110 extending from ring 108. Each arm 110 is configured to couple one spline 102 to ring 108 by piercing Kapton layers of spline 102, or using any other suitable coupling technique.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter, comprising:
a shaft for insertion into an organ of a patient;
an extendable distal-end assembly, which is coupled to the shaft and comprises multiple splines, wherein at least one spline comprises a flexible circuit board having one or more electrodes disposed thereon, wherein the circuit board is configured, when the distal-end assembly is extended in the organ, to conform to a surface of the organ so as to make contact between the electrodes and the surface; and
two or more strengthening elements, which are distributed along the circuit board of the spline and are configured to mechanically strengthen the spline, the strengthening elements comprise two or more blocks coupled to the circuit board and one or more solid elastic wedges, wherein each solid elastic wedge comprises a wedge shape member with a tapering thickness that is coupled between two adjacent blocks of said two or more blocks and is configured to force the spline to conform to the surface of the organ.

2. The catheter according to claim 1, wherein the strengthening elements comprise stripes coupled to the circuit board.

3. The catheter according to claim 1, wherein the electrodes are coupled to a side of the circuit board adapted to face the surface of the organ.

4. The catheter according to claim 1, wherein the strengthening elements are coupled to a side of the circuit board adapted to face away from the surface of the organ.

5. The catheter according to claim 1, wherein at least a pair of adjacent blocks" is changed to at least a pair of adjacent blocks of the two or more blocks comprises respective magnets that are positioned so as to magnetically repulse one another.

6. The catheter according to claim 1, wherein at least one of the two or more blocks has a trapezoid shape.

7. The catheter according to claim 1, wherein the blocks are made from aramid fiber-filled epoxy (AFEP).

8. The catheter according to claim 1, wherein the flexible circuit board is made from one or more layers of Kapton.

9. The catheter according to claim 1, wherein the catheter comprises a basket catheter.

10. A method for producing a catheter, the method comprising:
providing a spline, which comprises a flexible circuit board having one or more electrodes disposed thereon;
distributing along the circuit board of the spline two or more strengthening element, so as to mechanically strengthen the spline, the strengthening elements comprise two or more blocks coupled to the circuit board and one or more solid elastic wedges, wherein each solid elastic wedge comprises a wedge shape member with a tapering thickness that is coupled between two adjacent blocks of said two or more blocks and is configured to force the spline to conform outward;
producing an extendable distal-end assembly that comprises multiple splines, of which at least one of the splines comprises the spline; and
coupling the distal end assembly to a shaft for inserting the catheter into an organ of a patient.

11. The method according to claim 10, wherein at least a pair of adjacent blocks of the two or more blocks comprises respective magnets that are positioned so as to magnetically repulse one another.

12. The method according to claim 10, wherein at least one of the two or more blocks has a trapezoid shape.

13. The method according to claim 10, wherein the flexible circuit board is made from one or more layers of Kapton.

14. The method according to claim 10, wherein the catheter comprises a basket catheter.

\* \* \* \* \*